US012690824B2

(12) United States Patent
Hsieh

(10) Patent No.: US 12,690,824 B2
(45) Date of Patent: Jul. 28, 2026

(54) DYNAMIC CONTROL OF X-RAY EXPOSURE USING FOCAL SPOT TRANSLATION

(71) Applicant: Mayo Foundation for Medical Research and Education, Rochester, MN (US)

(72) Inventor: Scott S. Hsieh, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 266 days.

(21) Appl. No.: 18/710,059

(22) PCT Filed: Nov. 15, 2022

(86) PCT No.: PCT/US2022/049889
§ 371 (c)(1),
(2) Date: May 14, 2024

(87) PCT Pub. No.: WO2023/086658
PCT Pub. Date: May 19, 2023

(65) Prior Publication Data
US 2025/0025114 A1 Jan. 23, 2025

Related U.S. Application Data

(60) Provisional application No. 63/279,380, filed on Nov. 15, 2021.

(51) Int. Cl.
*A61B 6/03* (2006.01)
*A61B 6/00* (2006.01)
*G21K 1/02* (2006.01)

(52) U.S. Cl.
CPC .............. *A61B 6/03* (2013.01); *A61B 6/4447* (2013.01); *G21K 1/025* (2013.01)

(58) Field of Classification Search
None
See application file for complete search history.

(56) References Cited

U.S. PATENT DOCUMENTS 7,076,029 B2 7/2006 Toth et al.
7,330,535 B2 2/2008 Arenson et al.
(Continued)

OTHER PUBLICATIONS

Gang, G. et al., Dynamic Fluence Field Modulation in Computed Tomography Using Multiple Aperture Devices, Physics in Medicine & Biology, 2019, 64: 105024, pp. 1-13.
(Continued)

*Primary Examiner* — Twyler L Haskins
(74) *Attorney, Agent, or Firm* — Quarles & Brady LLP

(57) ABSTRACT

A method for acquiring x-ray data from a subject and generating a computed tomography (CT) image of the subject includes receiving a set of illumination field data including an illumination field produced by each of a plurality of focal spot positions of an x-ray source, selecting at least one sequence of at least two illumination fields based on at least one subject-specific parameter, assigning an illumination field from the selected at least one sequence to each gantry rotation angle in a plurality of gantry rotation angles, acquiring x-ray data from a subject for each gantry rotation angle using a focal spot position associated with the illumination field that is assigned to the gantry rotation angle, and generating an image slice based on the acquired x-ray data for each of the plurality of gantry rotation angles. The x-ray data can include a number of photons received by the detector array.

19 Claims, 5 Drawing Sheets

(56)　　　　References Cited

U.S. PATENT DOCUMENTS

| | | | |
|---|---|---|---|
| 9,392,984 B2 | 7/2016 | Pelc et al. | |
| 9,414,792 B2 | 8/2016 | Hsieh et al. | |
| 9,424,958 B2 | 8/2016 | Vogtmeier et al. | |
| 9,521,982 B2 | 12/2016 | Hsieh et al. | |
| 10,082,473 B2 | 9/2018 | Pack et al. | |
| 2011/0080992 A1* | 4/2011 | Dafni .................. | A61B 6/4014 |
| | | | 378/9 |
| 2018/0001111 A1 | 1/2018 | Stayman et al. | |

OTHER PUBLICATIONS

Gao, H. et al., Densely Sampled Spectral Modulation for X-ray CT Using a Stationary Modulator with Flying Focal Spot: A Conceptual and Feasibility Study of Scatter and Spectral Correction, Medical Physics, 2021, 48(4):1557-1570.

Hsieh, S. et al., The Feasibility of a Piecewise-Linear Dynamic Bowtie Filter, Medical Physics, 2013, 40(3):031910, pp. 1-12.

Hsieh, S. et al., Control Algorithms for Dynamic Attenuators, Medical Physics, 2014, 41(6):061907, pp. 1-17.

Huck, S. et al., Technical Note: Sheet-Based Dynamic Beam Attenuator—A Novel Concept for Dynamic Fluence Field Modulation in X-ray CT, Medical Physics, 2019, 46(12):5528-5537.

Petrongolo, M. et al., Single-Scan Dual-Energy CT Using Primary Modulation, IEEE Transactions on Medical Imaging, 2018, 37(8):1799-1808.

Stayman, J. et al., Grating-Based Spectral CT Using Small Angle X-ray Beam Deflections, In Conference Proceedings, International Conference on Image Formation in X-ray Computed Tomography, 2020, 2020:630-633.

Szczykutowicz, T. et al., Design of a Digital Beam Attenuation System for Computed Tomography: Part I. System Design and Simulation Framework, Medical Physics, 2013, 40(2):021905, pp. 1-12.

Xi, Y. et al., Grating Oriented Line-Wise Filtration (GOLF) for Dual-Energy X-ray CT, Sensing and Imaging, 2017, vol. 18, Article No. 27, https://doi.org/10.1007/s11220-017-0174-7, 32 pages.

PCT International Search Report and Written Opinion, PCT/US2022/049889, Feb. 21, 2023, 10 pages.

* cited by examiner

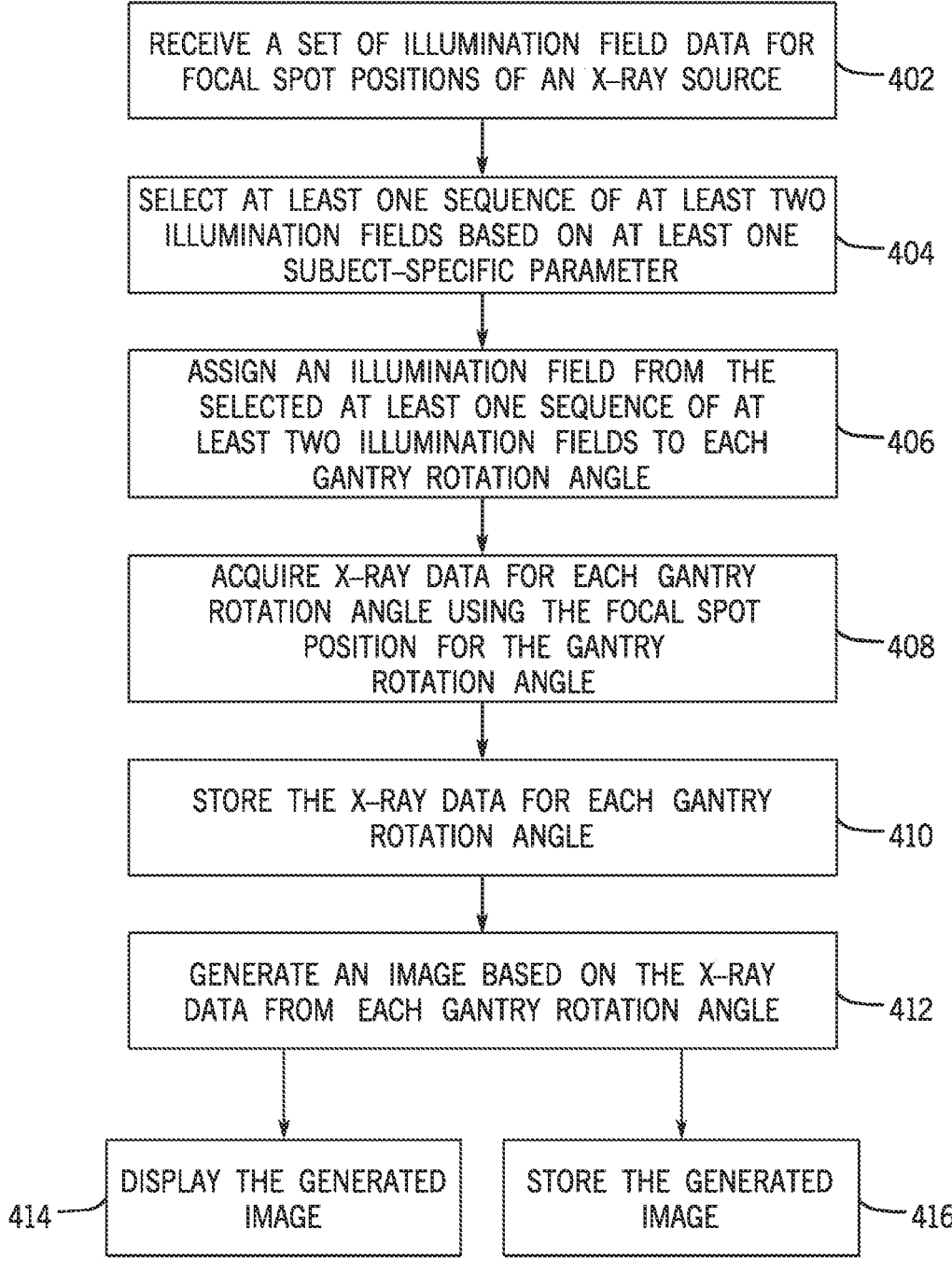

RECEIVE A SET OF ILLUMINATION FIELD DATA FOR FOCAL SPOT POSITIONS OF AN X-RAY SOURCE ~402

SELECT AT LEAST ONE SEQUENCE OF AT LEAST TWO ILLUMINATION FIELDS BASED ON AT LEAST ONE SUBJECT-SPECIFIC PARAMETER ~404

ASSIGN AN ILLUMINATION FIELD FROM THE SELECTED AT LEAST ONE SEQUENCE OF AT LEAST TWO ILLUMINATION FIELDS TO EACH GANTRY ROTATION ANGLE ~406

ACQUIRE X-RAY DATA FOR EACH GANTRY ROTATION ANGLE USING THE FOCAL SPOT POSITION FOR THE GANTRY ROTATION ANGLE ~408

STORE THE X-RAY DATA FOR EACH GANTRY ROTATION ANGLE ~410

GENERATE AN IMAGE BASED ON THE X-RAY DATA FROM EACH GANTRY ROTATION ANGLE ~412

414~ DISPLAY THE GENERATED IMAGE

STORE THE GENERATED IMAGE ~416

FIG. 4

DYNAMIC CONTROL OF X-RAY EXPOSURE USING FOCAL SPOT TRANSLATION

CROSS-REFERENCE TO RELATED APPLICATIONS

This application is based on, claims priority to, and incorporates herein by reference in its entirety U.S. Ser. No. 63/279,380 filed Nov. 15, 2021 and entitled "Dynamic Control of X-Ray Exposure Using Focal Spot Translation."

STATEMENT REGARDING FEDERALLY SPONSORED RESEARCH

N/A

BACKGROUND

X-ray computed tomography (CT) scanners are responsible for half of the manmade radiation to the U.S. population. While the carcinogenic risks of this radiation are not entirely known, it is desirable to reduce this radiation to the lowest possible levels. Currently, the x-ray illumination field emitted from a CT scanner is generic and cannot be personalized to the individual patient or examination. For example, CT scanners do not offer a good way to spatially modulate the dose delivered in a patient-specific manner. As a result, some regions may be over-illuminated and other under-illuminated, and the overall dose delivered may be more than necessary. While work has been done in the area of using dynamic filtration to reduce radiation, none of the existing technologies has been implemented on commercial scanners. Many of the prior dynamic filtration solutions present different trade-offs with respect to implementation complexity, magnitude of exposure reduction possible, and risk of imaging artifacts. For example, some prior dynamic filtration solutions utilize moving parts which are prone to failure and frequent maintenance downtime. Some prior dynamic filtration solutions are not able to provide enough dynamic control to achieve adequate exposure reduction (e.g., an average radiation dose reduction of 10% may be inadequate to satisfy justify a hardware redesign). Some prior solutions require the x-ray source to double in intensity which can be hard to achieve.

Thus, there remains a need for improved systems and methods for dynamic filtration for reducing the total radiation dose delivered to a patient in a patient-specific manner.

SUMMARY OF THE DISCLOSURE

In accordance with an embodiment, a method for acquiring x-ray data from a subject and generating a computed tomography (CT) image of the subject includes receiving, using a processor device, a set of illumination field data including an illumination field produced by each of a plurality of focal spot positions of an x-ray source, selecting, using the processor device, at least one sequence of at least two illumination fields from the set of illumination field data based on at least one subject-specific parameter; assigning an illumination field from the selected at least one sequence of at least two illumination fields to each gantry rotation angle in a plurality of gantry rotation angles, and acquiring x-ray data from a subject, using a detector array, for each gantry rotation angle in the plurality of gantry rotation angles using a focal spot position associated with the illumination field that is assigned to the gantry rotation angle. The x-ray data can include a number of photons received by the detector array. The method further includes generating an image slice, using the processor device, based on the acquired x-ray data for each of the plurality of gantry rotation angles.

In accordance with an embodiment, a system for acquiring x-ray data for a computed tomography (CT) image of a subject includes an x-ray source comprising an actuator system configured to energize one of a plurality of focal spot positions, a grid assembly positioned in front of the x-ray source and comprising a plurality of grids, wherein each grid comprises a plurality of attenuating objects and a processor device coupled to the x-ray source. The processor device may be programmed to receive a set of illumination field data including an illumination field produced by each of the plurality of focal spot positions of the x-ray source, select at least one sequence of at least two illumination fields from the set of illumination field data based on at least one subject-specific parameter and assign an illumination field from the selected at least one sequence of at least two illumination fields to each gantry rotation angle in a plurality of gantry rotation angles. The system further includes a detector array configured to receive x-ray data from the subject for each gantry rotation angle in the plurality of gantry rotation angles. The x-ray data for each gantry rotation angle is based on the illumination field assigned to the gantry rotation angle and produced by an energized focal spot position associated with the assigned illumination field. The x-ray data can include a number of photons received by the detector array.

In accordance with an embodiment, a system for acquiring x-ray data for a computed tomography (CT) image of a subject, the system includes an x-ray source comprising an actuator system configured to energize one of a plurality of focal spot positions, a slot collimator positioned in front of the x-ray source and comprising an opening having a width and a processor device coupled to the x-ray source. The processor device may be programmed to receive a set of illumination field data including an illumination field produced by each of the plurality of focal spot positions of the x-ray source, select at least one sequence of at least two illumination fields from the illumination field data based on at least one subject-specific parameter, and assign an illumination field from the selected at least one sequence of at least two illumination fields to each gantry rotation angle in a plurality of gantry rotation angles. The system further includes a detector array configured to receive x-ray data from the subject for each gantry rotation angle in the plurality of gantry rotation angles. The x-ray data for each gantry rotation angle is based on the illumination field assigned to the gantry rotation angle and produced by an energized focal spot position associated with the assigned illumination field. The x-ray data can include a number of photons received by the detector array.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 4 illustrates a method for adjusting an illumination field for acquiring x-ray data and generating an image using an x-ray computed tomography (CT) system in accordance with an embodiment.

DETAILED DESCRIPTION

Figure 1:
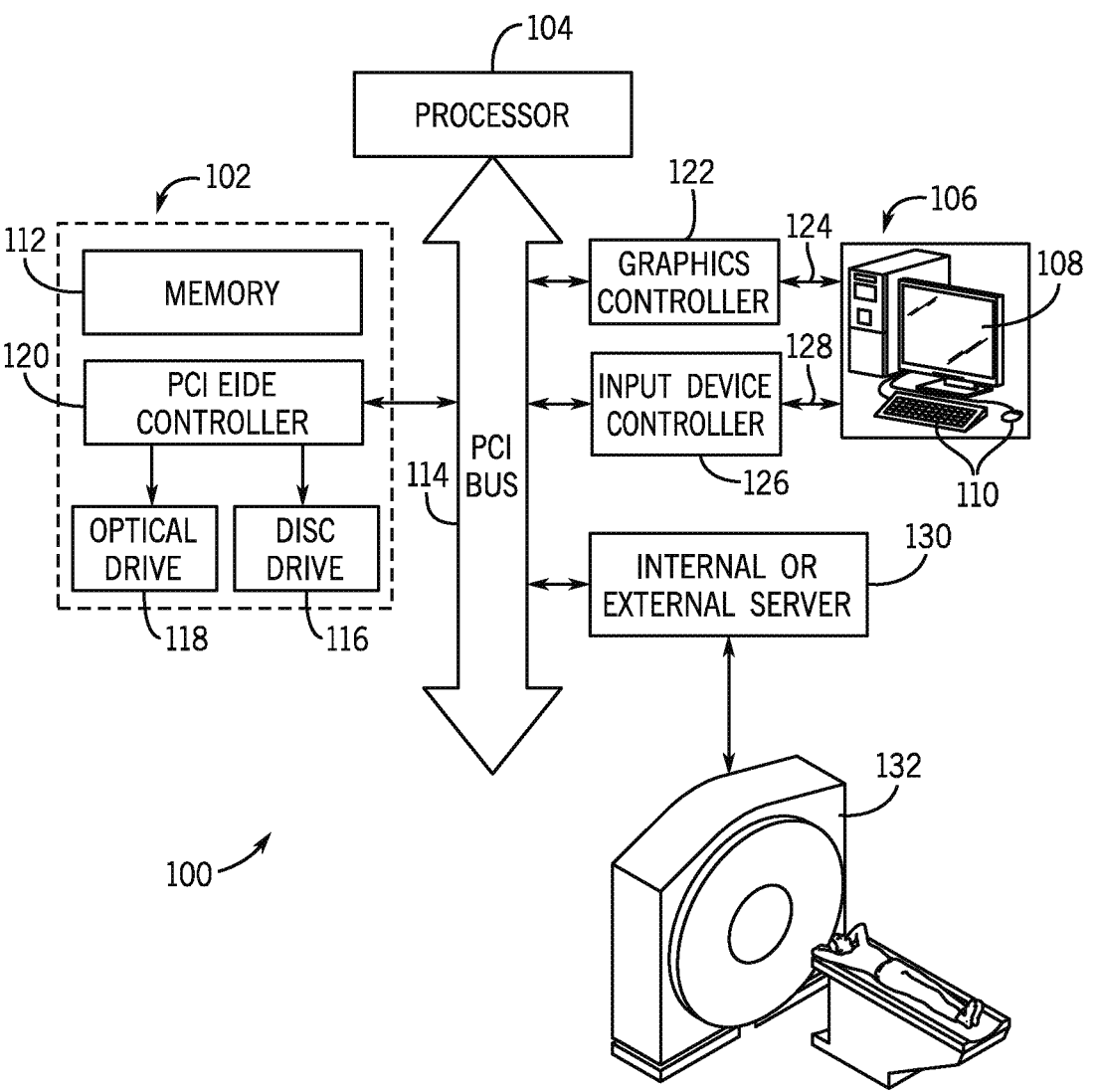
FIG. 1 is a block diagram of a computer system in accordance an embodiment.

The present disclosure describes systems and methods for dynamically adjusting an illumination field (or equivalently, adjusting the exposure field, fluence field, or x-ray filtration) for acquiring x-ray data from a subject for computed tomography (CT) imaging. In some embodiments, a desired illumination field is achieved by selecting one of a plurality of discrete focal spot positions (or locations) to energize for a gantry rotation angle (or view) in an acquisition of x-ray data for a CT image (e.g., a slice). In some embodiments, at least one sequence of at least two focal spot positions (and the illumination field associated with each focal spot position) may be selected for an acquisition of x-ray data from a particular subject and one of the at least two focal spot positions (and the associated illumination field for the one focal spot position) from the at least one selected sequence may be assigned to each gantry rotation angle. Accordingly, the illumination fields and focal spot positions for an acquisition may be tailored for each subject being scanned. In some embodiments, the sequence or sequences of illumination fields (and corresponding focal spot positions) for a scan of a subject may be selected based on a set of parameters or characteristics for subject-specific exposure (or dose) and image quality objectives for the scan, such as, for example, organ radiation exposure (or dose), photon statistics, overall effective dose, region of interest, and the like. In some embodiments, the systems and methods may dynamically select from the fixed focal spot positions (and associated illumination fields) for each new gantry rotation angle, for example, to dynamically adjust image quality during an acquisition (or scan). Advantageously, the disclosed systems and methods can minimize radiation exposure while maintaining image quality.

In some embodiments, the system for dynamically adjusting an illumination field can include an x-ray source that can be configured to energize one of a plurality of discrete focal spot positions (or locations), a grid assembly (or x-ray interference field) positioned in front of the x-ray source, and a processor device (or computer system) that can be configured to select one of the plurality of focal spot positions for each gantry rotation angle to achieve the desired x-ray illumination field for an acquisition of an image slice. The x-ray source may include an electromagnetic actuator system to energize a selected focal spot position. The grid assembly may include two or more grids (or layers). In some embodiments, the system for dynamically adjusting an illumination field can include, a slot collimator positioned in front of the x-ray source instead of a grid assembly. Advantageously, the systems for adjusting an illumination field described herein do not require moving parts to select and energize one of the plurality of focal spot positions for a gantry rotation angle of the acquisition. The described systems and methods can also reduce calibration complexity and enable sophisticated fluence modulation.

Referring now to FIG. 1, a computer system 100 that can perform the methods described in the present disclosure is illustrated. In general, the computer system 100 may include a memory workstation 102, a processor 104, and an operator workstation 106 that may include a display 108 and one or more input devices 110 (e.g., keyboard, a mouse, a touch screen).

The processor 104 may be a commercially available programmable machine running on a commercially available operating system. For example, the processor 104 may include internal memory and I/O control to facilitate system integration and integral memory management circuitry for handling all external memory 112. The processor 104 may also have access to a peripheral component interconnect (PCI) bus driver that facilitates interfacing with a PCI bus 114. The processor 104 may operate autonomously or semi-autonomously. The processor 104 may read executable software instructions from the memory 112, or a computer-readable medium (e.g., disc drive 116, optical drive 118, hard drive, flash memory). The processor 104 may also receive instructions via the one or more input devices 110 from the user, or another source logically connected to a computer or device, such as another networked computer or server.

The PCI bus 114 may be an industry standard bus that transfers data between the processor 104 and a number of peripheral controller cards. These may include a PCI enhanced integrated drive electronics (EIDE) controller 120 which provides a high-speed transfer of data to and from an optical drive 118 (e.g., CD-ROM drive) and a disc drive 116. A graphics controller 122 may be used to couple the PCI bus 114 to the display 108 through a standard display connection 124, and an input device controller 126 may receive data from the one or more input devices 110, such as a mouse or a keyboard, through respective connection 128.

In some embodiments, the display 108 may be a monitor, which presents a graphical user interface (GUI) that allows a user to input parameters into the workstation 106. The input parameters may take any suitable shape or form, as desired, for operation of the computer system 100, including the ability for selecting, entering, or otherwise specifying parameters consistent with processing tasks, processing data, or operating the computer system 100. The computer system 100 may receive data, such as medical imaging data, from an internal or external server 130, for example, from a department picture archiving and communications system (PACS), an institution image management system, or other source capable of transferring medical imaging data. In some embodiments the computer system 100 may be directly connected to a medical imaging system 132, such as an x-ray computed tomography ("CT") imaging system, for example, the system described in FIGS. 2A and 2B.

In some embodiments, the computer system 100 can be implemented, for example, by a workstation, a notebook computer, a tablet device, a mobile device, a multimedia device, a network server, a mainframe, one or more controllers, one or more microcontrollers, or any other general-purpose or application-specific computing device.

Figure 2A:
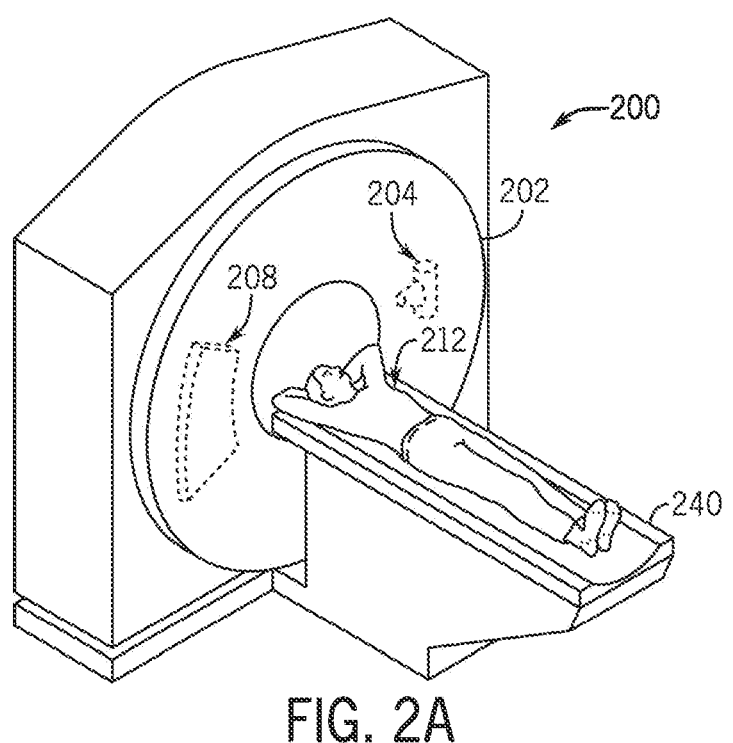
FIG. 2A is an illustration of an x-ray computed tomography (CT) imaging system in accordance with an embodiment.
Figure 2B:
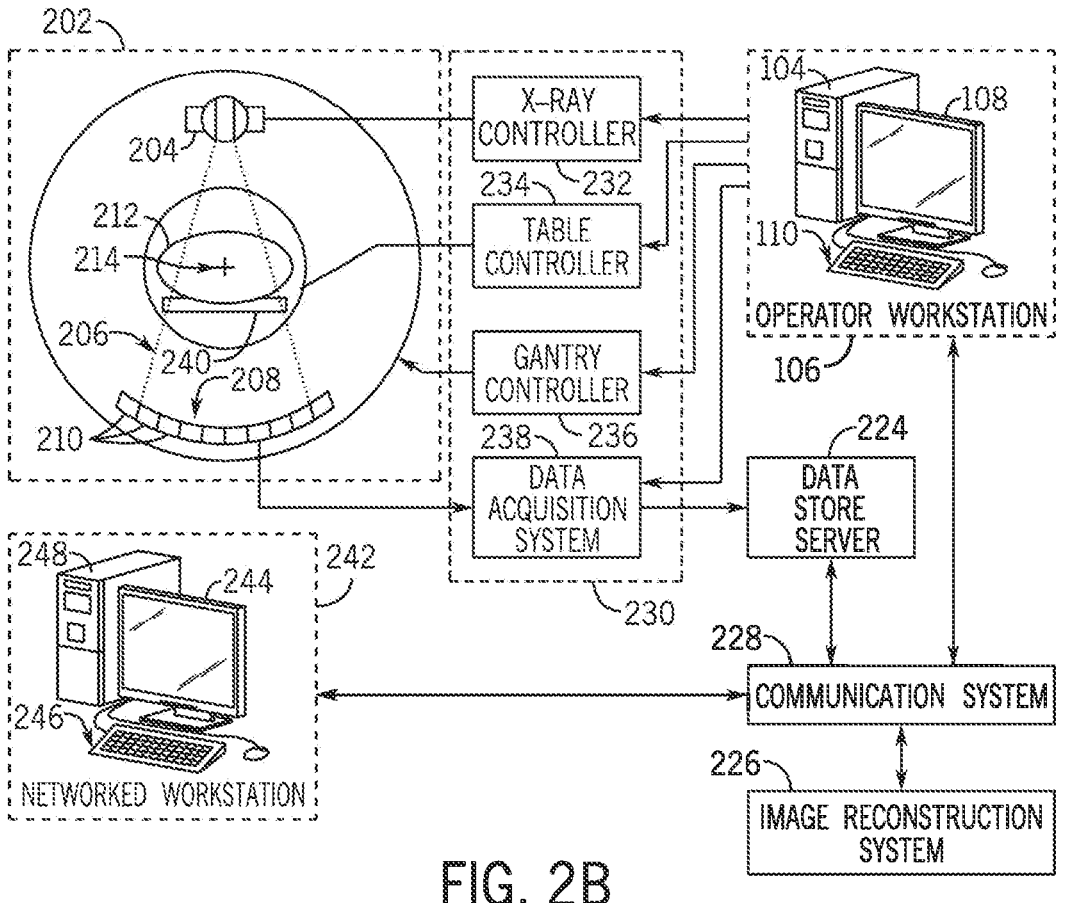
FIG. 2B is a block diagram of the CT imaging system of FIG. 2A in accordance with an embodiment.

Referring particularly now to FIGS. 2A and 2B, an example of an x-ray CT imaging system 200 that may be used to implement the methods in accordance with the present disclosure. The CT system may include a gantry 202, to which at least one x-ray source 204 may be coupled. The x-ray source 204 can project an x-ray beam 206, which may be a fan-beam or cone-beam of x-rays, towards a detector array 208 on the opposite side of the gantry 202. The detector array 208 can include a number of x-ray detector elements 210. Together, the x-ray detector elements 210 can sense the projected x-rays 206 that pass through a subject 212, such as a medical patient or an object undergoing examination, that is positioned in the CT system 200. Each x-ray detector element 210 can produce an electrical signal that may represent the intensity of an impinging x-ray beam and, hence, the attenuation of the beam as it passes through the subject 212. In some configurations, each x-ray detector 210 may be capable of counting the number of x-ray photons that impinge upon the detector 210. During a scan to acquire x-ray projection data, the gantry 202 and the components mounted thereon can rotate about a center of rotation 214 located within the CT system 100.

The CT system 200 can also include an operator workstation 106, which typically includes the display 108; one or input devices 110, such as a keyboard and mouse; and a computer processor 104, for example, as described in FIG. 1. The operator workstation 106 can provide the operator interface that enable scanning control parameters to be entered into the CT system 200. In general, the operator workstation 106 may be in communication with a data store server 224 and an image reconstruction system 226. By way of example, the operator workstation 106, data store server 224, and image reconstruction system 226 may be connected via a communication system 228, which may include any suitable network connection, whether wired, wireless, or combination of both. As an example, the communication system 228 may include both proprietary or dedicated networks, as well as open networks, such as the Internet.

The operator workstation 106 may also be in communication with a control system 230 that can control operation of the CT system 200. The control system 230 generally can include an x-ray controller 232, a table controller 234, a gantry controller 232, and a data acquisition system (DAS) 238. The x-ray controller 232 can provide power and timing signals to the x-ray source 204 and the gantry controller 236 can control the rotational speed and position of the gantry 202. The table controller 234 can control a table 240 to position the subject 212 in the gantry 202 of the CT system 200.

The DAS 238 can sample data from the detector elements 210 and can convert the data to digital signals for subsequent processing. For instance, digitized x-ray data may be communicated from the DAS 238 to the data store server 224. The image reconstruction system 226 can then retrieve the x-ray data from the data store server 224 and can reconstruct an image therefrom. The image reconstruction system 226 may include a commercially available computer processor, or may be a highly parallel computer architecture, such as a system that includes multiple-core processors and massively parallel high-density computing devices. Optionally, image reconstruction can also be performed on the processor 104 in the operatory workstation 106. Reconstructed images can then be communicated back to the data store server 224 for storage or to the operator workstation 106 to be displayed to the operator or clinician.

The CT system 200 may also include one or more networked workstations 242. By way of example, a networked workstation 242 may include a display 244; one or more input devices 246, such as a keyboard and mouse; and a processor 248. The networked workstation 242 may be located within the same facility as the operator workstation 106, or in a different facility, such as a different healthcare institution or clinic.

The networked workstation 242, whether within the same facility or in a different facility as the operator workstation 106, may gain remote access to the data store server 224 and/or the image reconstruction system 226 via the communication system 228. Accordingly, multiple networked workstations 242 may have access to the data store server 224 and/or image reconstruction system 226. In this manner, x-ray data, reconstructed images, or other data may be exchanged between the data store server 224, the image reconstruction system 226, and the networked workstations 242, such that the data or images may be remotely processed by a networked workstation 242. This data may be exchanged in any suitable format, such as in accordance with the transmission control protocol ("TCP"), the internet protocol ("IP"), or other known or suitable protocols.

As mentioned above, the x-ray source 204 can project an x-ray beam towards the detector array 208. During a scan, the gantry 202 and the components mounted thereon can rotate about the center of rotation (or isocenter) 214. As the gantry 202 (and the x-ray source 204) rotate about the center of rotation 214, the x-ray source can project an x-ray beam at various positions (e.g., angles of rotation of the gantry 202 and x-ray source 204) to acquire x-ray data. The x-ray data captured by the detector array 208 from the x-ray beam projected at a particular position of the x-ray source 204 and gantry rotation angle may also be referred to as a view. During a single rotation, a plurality of views (corresponding to a plurality of gantry rotation angles) may be acquired. In many third-generation CT scanners, the term "view" is used to refer to a single x-ray projection image acquired from a single gantry rotation angle, with successive views acquired in approximately uniform spacing in both time and gantry rotation angle. However, in systems with focal spot motion, "view" can also be used to refer to rebinned projections with higher readout. For clarity, as used herein, the term "view" refers to a single x-ray projection image acquired from a single gantry rotation angle. The x-ray data for the plurality of views from a single rotation may then be used to reconstruct a 2D image slice of the subject, for example, with the reconstruction using the gantry rotation angles together with the focal spot positions (or locations) in order to ascertain the correct geometry. During a scan, a plurality of rotations of the gantry 202 (and x-ray source 204) may be performed to produce a plurality of image slices of the subject.

In some embodiments, the x-ray source 204 may include an electromagnetic actuator system such as, for example, a flying focal spot (FFS) system. An electromagnetic actuator system uses electromagnets (e.g., located in the x-ray source 204) to deflect the beam of electrons from a cathode in the x-ray source 204 to a specific position, the focal spot, on an anode of the x-ray source 204. The focal spot receives the beam of electrons from the cathode and is the apparent source of the x-rays beam from the x-ray source. In some embodiments, the x-ray source may be configured to include a plurality of focal spot positions and the electromagnetic actuator system may be controlled to energize a particular focal spot position of the x-ray source to provide an illumination field for a particular gantry rotation angle as described further below. In addition, in some embodiments, a grid assembly may be positioned in front of the x-ray source 204 to provide an x-ray interference field that interacts with the x-ray beam produced by the x-ray source to produce an illumination field. The grid assembly may be configured to produce different illumination fields from each of the different focal spot positions of the x-ray source 204 as shown in FIGS. 3A and 3B.

Figure 3B:
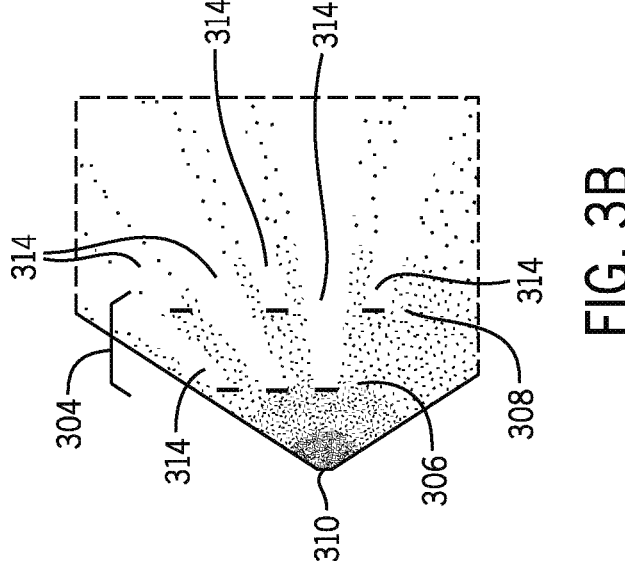
FIG. 3B illustrates an example grid assembly and a second focal spot position in accordance with an embodiment.
Figure 3A:
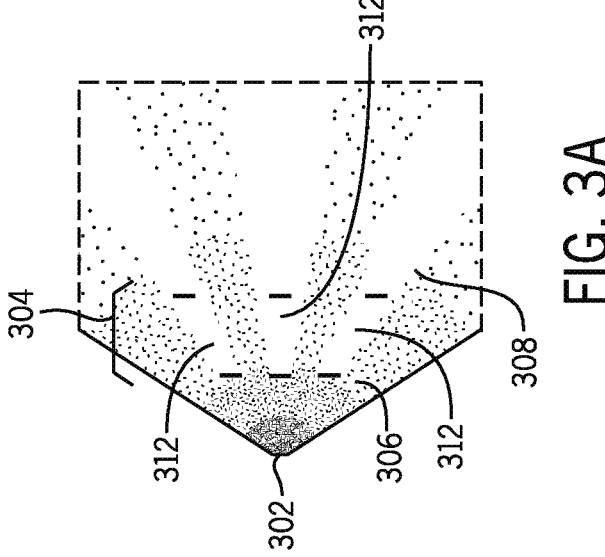
FIG. 3A illustrates an example grid assembly and a first focal spot position in accordance with an embodiment.

FIG. 3A illustrates an example grid assembly and a first focal spot position in accordance with an embodiment and FIG. 3B illustrates an example grid assembly and a second focal spot position in accordance with an embodiment. FIG. 3A shows a first focal spot position 302 (also referred to herein as "focal spot position A") and a grid assembly 304 positioned in front of the x-ray source. FIG. 3B shows a second focal spot position 310 (also referred to herein as "focal spot position B") and the grid assembly 304. In some embodiments, an electromagnetic actuator system may be used to energize either the first focal spot position 302 or the second focal spot position 310. The example grid assembly 304 illustrated in FIGS. 3A and 3B includes a first grid 306 (or first layer) and a second grid 308 (or second layer). While the example grid assembly 304 shown in FIGS. 3A and 3B includes two grids, it should be understood that in various embodiments the grid assembly can include two or more grids. Additionally, there may be more than two focal spot positions. The first grid (or first layer) 306 and the second grid (or second layer) 308 may each include a plurality of attenuating objects (e.g., gold or tungsten) which are highly radio-opaque interspersed with a spacer (e.g., air or plastic) that is transmissive. In FIGS. 3A and 3B, the attenuating objects in each grid 306 and 308 are represented by the black lines. In some embodiments, one or more of the grids 306 and 308 may include focused lamellae that are directed towards a focal spot. The grids 306 and 308 in the grid assembly 304 may be arranged or lined up so that depending on the focal spot position (e.g., the first focal spot position 302 or the second focal spot position 310), more or less attenuating is generated. For example, in FIGS. 3A and 3B, the grid assembly 304 includes two planar grids (306, 308) that are arranged such that the attenuating objects in the first grid (or first layer) 306 overlap the attenuating objects in the second grid (or second layer) 308.

In FIG. 3A, the first focal spot position 302 is selected and the regions 312 denote radiation from the x-ray source (i.e., first focal spot position 302) that is blocked by the grid assembly 304. Accordingly, the first focal spot position 302 and grid assembly 304 produce a first illumination field. In FIG. 3B, the second focal spot position 310 is selected and the regions 314 denote radiation from the x-ray source (i.e., second focal spot position 302) that is blocked by the grid assembly 304. The second focal spot position 310 and grid assembly 304 produces a second illumination field different from the first illumination field. In the second illumination field shown in FIG. 3B, more radiation from the x-ray source can be blocked because more of the grid assembly 304 is exposed. While the examples shown in FIGS. 3A and 3B illustrate two focal spot positions and two illumination fields, it should be understood that in various embodiments different numbers of focal spot positions and grids can be used to produce different numbers of different illumination fields.

In some embodiments, the grid assembly 304 may be designed to produce a particular illumination field (or fluence field) using each focal spot position 302, 310 based on various parameters of the x-ray source and focal spot position. In the following example design of the grid assembly 304 to produce the illumination fields for the first focal spot position 302 and the second focal spot position 310, to simplify the discussion, it is assumed that the first grid 306 and the second grid 308 are formed from tungsten bars and plastic spacer, that the tungsten bars are perfectly blocking, that the plastic spacer is perfectly transmissive, and that the first grid 306 and the second grid 308 of the grid assembly 304 are two planar layers. In addition, the example is discussed using representative geometric distances. In this example, Layer 1 (first grid 306) and Layer 2 (second grid 308) are at distance $d_1=100$ mm, $d_2=120$ mm from the focal spot (302 or 310). Within each layer 306, 308, the tungsten bars can have a characteristic center-to-center periodicity between bars. In this example, the periodicity of the first layer 206 is p=1 mm and the periodicity of the second layer 308 is $d_2/d_1$ times larger, so that the apparent periodicity of both layers when seen from the detector is identical. The width of the bars in the first layer 306 can be a smooth function $w_1(\gamma)$, where $\gamma$ is the fan angle. In the second layer 308, the width of the bars is a separate function $w'_2(\gamma)$. In this example, $w_2(\gamma)$ is defined as $$w_2(\gamma) = \frac{d_1}{d_2} w'_2(\gamma),$$

so that the fraction of photons blocked by the first layer 306 or the second layer 308 in isolation are $w_1(\gamma)/p$ and $w_2(\gamma)/p$, respectively.

In the example shown in FIGS. 3A and 3B, there are two focal spot positions 302, 310 that may be selected for excitation. For each gantry rotation angle, the system can select from focal spot position A 302 or focal spot position B 310. The bars of the second layer 308 may be positioned so that they are in the shadow of the bars in the first layer 306 from the perspective of focal spot position A 302, but are exposed (halfway in between the bars of the first layer 306) from focal spot position B 310. Using similar triangles, this example arrangement requires that the distance between focal spot positions A 302 and B 310, $\Delta_{AB}$, must satisfy the geometric constraint that:

$$\frac{(d_1 - d_2)}{d_2} \Delta_{AB} = \frac{kp}{2} \qquad \text{Eq. 1}$$

where k is an odd integer. For k=−1, it is found that $\Delta_{AB}=3$ mm. Finally, it can be required that $w_2(\gamma) < w_1(\gamma) - \epsilon$, where $\epsilon$ is a positive value and greater values of $\ominus$ create more stability with respect to x-ray source position perturbation. This ensures that the second layer 308 is fully shadowed by the first layer 306 in focal spot position A 302 even in the presence of mechanical vibration, nonzero size of the focal spot, or actuator noise. The fluence field from focal spot position A 302 may therefore be determined by the first layer 306 alone:

$$I_A(\gamma) = I_0 \left( 1 - \frac{w_1(\gamma)}{p} \right) \qquad \text{Eq. 2}$$

with $I_0$ being the raw intensity of the x-ray beam. Finally, assuming that $w_1(\gamma) + w_2(\gamma) < 1$, the fluence field from Position B is:

$$I_B(\gamma) = I_0 \left( 1 - \frac{w_1(\gamma) + w_2(\gamma)}{p} \right) \qquad \text{Eq. 3}$$

where the widths of the two layers are effectively additive.

In some embodiments, choosing p smaller than 1 mm may reduce high-frequency variation in the fluence field and subsequent ring artifacts. As mentioned above, more than two focal spot positions and more than two layers can be used and may lead to more flexible x-ray illumination field modulation. For example, with four layers, one can have a focal spot position (or location) where only the first layer (or grid) is seen because the rest are hidden; another focal spot position where layers (or grids) 1-4 are all seen separately; and anther position where the first layer (or grid) and the second layer (or grid) are exposed, but the third and fourth layers (or grids) are both hidden, and so on.

In some embodiments, other solutions for equation 1

$$\left( \frac{d_2 - d_1}{d_2} \Delta_{AB} = \frac{kp}{2} \right)$$

may be selected and accordingly, focal spot positions may be selected that are essentially steered alternatives. This can be used, for example, to accommodate off-centered patients or complex objectives such as sending radiation to two opposite sectors of the subject. In some embodiments, with three layers (or grids) and five steering options (i.e., five focal spot positions), it can be possible to create 15 potential focal spot positions (or locations) which can be selected for a particular gantry rotation angle. In this example, an x-ray source would be required that was configured with a wide range of electromagnetic travel.

In some embodiments, the x-ray source and electromagnetic actuator system may be configured to spend a variable length of time on the first focal spot position A 302 and the second focal spot position B 310. As mentioned, when the x-ray source dwells at first focal spot position A 302 and second focal spot position B 310, the grid assembly 304 is configured to interact with the x-ray source to produce an illumination field f(A) and f(B), respectively. In this example, the electromagnetic actuator system can spend a fraction of time, t, at the focal spot position A 302, and a remaining fraction of time 1-*t* at focal spot position B 310. In some embodiments, the fraction t changes through the course of the scan. The resulting x-ray exposure can be expressed as t*f(A)+(1−t)*f(B). This type of system can require variable readout time on the detector. Accordingly, in some embodiments, adjustment of an illumination field may further be varied by adjusting a duration of time at a focal spot position for a gantry rotation angle.

As mentioned above, a processor device (or computer system), for example, processor 104 (shown in FIGS. 1 and 2B) may be configured to select one of a plurality of discrete focal spot positions (or locations) of an x-ray source to dynamically control or adjust the illumination field (or fluence field or illumination profile) for each gantry rotation angle in order to achieve a desired subject-specific x-ray illumination field for an acquisition of x-ray data for an image slice and for an entire CT scan. FIG. 4 illustrates a method for adjusting an illumination field for acquiring x-ray data and generating an image using an x-ray computed tomography (CT) system in accordance with an embodiment. At block 402, a set of illumination field data for a plurality of focal spot positions (or locations) of an x-ray source of the CT system used for a scan of a subject is received. In some embodiments, the set of illumination field data includes an illumination field (or illumination profile) produced by each of the focal spot positions of the x-ray source (e.g., x-ray source 204 shown in FIGS. 2A and 2B).

In some embodiments, the illumination field produced by each focal spot position may be determined during a calibration process for the CT system and stored in data storage such as, for example, memory of a processor 104, memory 112 of computer system 100, or other computer memory. For example, a grid assembly (e.g., grid assembly 304) and the plurality of focal spot positions of the x-ray source can be used to produce a series of N possible illumination fields, $I_1$, $I_2$, $I_N$. As discussed above, each illumination field corresponds to a distinct focal spot position, 1–N. In some embodiments, known methods for determining the illumination field for a focal spot position of an x-ray source may be used. In some embodiments, the method used to determine the illumination field for each focal spot position can incorporate the effects of finite attenuation.

At block 404, at least one sequence of at least two illumination fields (and the associated focal spot positions) may be selected from the set of illumination field data based on at least one subject-specific parameter. For example, the sequence of two or more illumination fields that best achieves the subject-specific parameter(s) may be selected. In some embodiments, the one or more sequences of at least two illumination fields may be selected from a plurality of sequences of at least two illumination fields formed from different possible combinations of the N possible illumination fields, $I_1$, $I_2$, $I_N$. In some embodiments, the at least one subject specific parameter can be a parameter or characteristic associated with subject-specific exposure (or dose) and image quality objectives for the scan, such as, for example, organ radiation exposure (or dose), photon statistics (e.g., number of photons that reach a detector), overall effective dose, region of interest, and the like. The subject-specific parameters and characteristics may be, for example, determined on the fly (e.g., image quality), determined based on scout images (e.g., lateral and A/P x-ray projections), determined based on a low-dose volumetric pre-scan, received from operator input, determined using heuristics to predict expected regions of heightened dose sensitivity such as, for example, radiation directly illuminating the eye lens or the breast, predetermined, etc. The subject-specific parameters or characteristics may be stored in data storage such as, for example, memory of a processor 104, memory 112 of computer system 100, or other computer memory. In some embodiments, a score may be generated for each of a plurality of sequences of at least two illumination fields $I_1$, $I_2$, . . . . $I_N$, based on one or more of the subject-specific parameters. In some embodiments, the score may be configured to incorporate the ability of a particular sequence of illumination fields to achieve an image quality and radiation exposure objective for the image slice and the entire CT scan.

At block 406, an illumination field (and the corresponding focal spot position) from the selected sequence(s) of two of more illumination fields is assigned to each gantry rotation angle for the acquisition of an image slice. For example, assuming N>5, an example sequence (or combination) of four illumination fields may be $2*I_1+I_3+I_5$, namely, a sequence of a first illumination field ($I_1$), the first illumination field ($I_1$), a third illumination field ($I_3$) and a fifth illumination field ($I_5$). If the example sequence of four illumination fields $2*I_1+I_3$, $+I_5$ is selected based on one or more subject-specific parameters, the first illumination field $I_1$ (associated with a first focal spot position) may be assigned to a first gantry rotation angle, the first illumination field $I_1$ (associated with the first focal spot position) may be assigned to a second gantry rotation angle, the third illumination field $I_3$ (associated with a third focal spot position)

may be assigned to the third gantry rotation angle, and the fifth illumination field Is (associated with a fifth focal spot position) may be assigned to a fourth gantry rotation angle. In some embodiments, the same sequence may be assigned to the next four gantry rotation angles in the acquisition, and so on until each gantry rotation angle of the acquisition has an assigned illumination field (and an associated focal spot position). In some embodiments, the sequence can change to accommodate the patient anatomy, including areas with poor photon statistics and areas that are dose-sensitive, as seen from different gantry angles. For example, the second four gantry rotation angles may be assigned an illumination field from a second selected sequence such as, for example, a second sequence of four illumination fields $I_1 + I_3, + I_3 + I_5$. As discussed further below, at each gantry rotation angle, the assigned illumination field and focal spot position may be used to acquire data for the gantry rotation angle.

At block 408, x-ray data can be acquired for each gantry rotation angle (e.g., using CT imaging system 200 shown in FIGS. 2A and 2B) using the assigned (or selected) focal spot position (and corresponding illumination field) of the x-ray source (e.g., x-ray source 204) for the gantry rotation angle. For example, for the example sequence of four illumination fields $2*I_1 + I_3, + I_5$ discussed above, x-ray data for a first gantry rotation angle is acquired by moving the focal spot to a first focal spot position to generate a first illumination field $(I_1)$, x-ray data for a second gantry rotation angle is acquired using the first focal spot position to generate the first illumination field $(I_1)$, x-ray data for a third gantry rotation angle is acquired by moving the focal spot to a third focal spot position to generate a third illumination field $(I_3)$, and x-ray data for a fourth gantry rotation angle is acquired by moving the focal spot to a fifth focal spot position to generate a fifth illumination field $(I_5)$. In some embodiments, the x-ray data may include photon statistics such as, for example, the number of photons received by the detector array, for example, at each gantry rotation angle.

At block 410, the x-ray data acquired for each gantry rotation angle may be stored in data storage, for example, data store server 224 of a CT imaging system 200 or other computer memory (e.g., memory 112 of computer system 100). At block 412, the acquired x-ray data for each gantry rotation angle may be used to generate or reconstruct an image (e.g., a 2D image slice) using known reconstruction methods. For example, an image reconstruction server 226 or other computer system (e.g., a processor 104 of an operator workstation 106) may be configured to reconstruct an image slice. In some embodiments, an image slice may be reconstructed using an algorithm that can accommodate nonuniform statistics and sampling, for example, statistical iterative reconstruction or rebinning. Advantageously, generating (or reconstructing) and image using x-ray data acquired by alternating between the illumination fields in the selected sequence, an effective weighted average of the discrete illumination fields may be achieved that satisfies the subject-specific parameters and objectives such as, for example, dose reduction. In some embodiments, an image may be generated from a combination of the x-ray data from the focal spot positions for each repetition of the selected sequence of illumination fields. For example, for the example sequence of four illumination fields $2*I_1 + I_3, + I_5$ discussed above, a first rebinned image may be generated from the x-ray data for the first four gantry rotation angles assigned to the sequence, a second rebinned image may be generated from the next four gantry rotation angles assigned to the sequence, and so on. In some implementations of conventional flying focal spot, the geometry may be chosen so that the rebinned data interlace perfectly to increase resolution. In the present disclosure, in some embodiments, the geometry cannot always be chosen in such a fashion, and so data from several more gantry rotation angles may be integrated together to produce the generated rebinned images. These rebinned images can also accommodate the variable photon statistics associated with the different illumination fields in order to create the weighted average. At block 414, the generated image slice may be displayed on a display (e.g., display 108 of operator workstation 106). The generated image may also be stored, at block 416, in data storage (e.g., data store server 224. In some embodiments the process of blocks 402-412 may be repeated to generate additional image slices during a CT scan. In some embodiments, a plurality of 2D image slices may be used to reconstruct a 3D CT image of the subject.

While the above description of FIG. 4 refers to an example of four illumination fields (and corresponding focal spot positions) in a sequence (or combination), in some embodiments the number of illumination fields that can be selected for a sequence depends on the reconstruction algorithm and the sampling rate of the detector array. With diverse options for illumination profiles $I_k$ and the ability to add different permutations of at least 4 of $I_k$, it may be possible to produce very complex illumination profiles.

It should be understood that the number of illumination fields present in a sequence (or combination) is an illustrative concept and it may not be necessary to specify an exact number with statistical reconstruction algorithms. In FFS, one may describe a combination of 2 views in z-FFS or 4 views in FFS that oversamples in both z and x axes. Analytic reconstruction algorithms can combine data from these 2 or 4 views into higher resolution views which may be used in higher resolution reconstruction. However, model-based iterative statistical reconstruction algorithms could directly work with the underlying data also without analytic rebinning. In the same way, while a combination of 4 views may be used, and while an analytic reconstruction algorithm could rebin 4 views into 1 higher resolution view, an iterative reconstruction can make use of the underlying data directly and it may be possible to use a combination of 3 views with an average illumination field that is desirable for dose reduction followed by a combination of 4 views with an average illumination field that is desirable for dose reduction.

Figure 5:
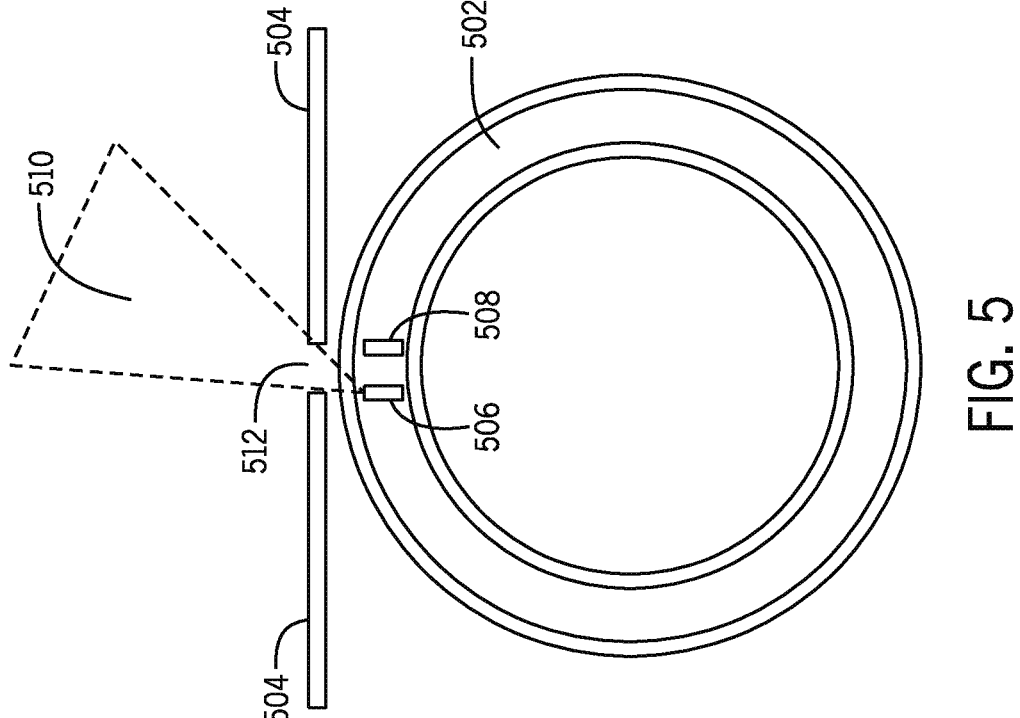
FIG. 5 illustrates an apparatus for adjusting an illumination field in accordance with an embodiment.

FIG. 5 illustrates an apparatus for adjusting an illumination field in accordance with an embodiment. An alternative system for modulating the flux in an x-ray CT system is shown in FIG. 5. In FIG. 5, two concentric circles 502 represent a focal track of an anode in an x-ray source (e.g., x-ray source 204 shown in FIGS. 2A and 2B). In the illustrated embodiment, a first focal spot position 506 and a second focal spot position 508 are drawn as rectangles that are elongated in the vertical direction due to the line focus principle. As discussed above, an x-ray source may include an electromagnetic actuator system such as, for example, flying focal spot (FFS). In some embodiments, only one of the focal spot positions 506, 508 may be energized at a time.

In some embodiments, a slot collimator 504, including a slot 512 having a width, is positioned directly adjacent to the focal track 502. The collimator can be made up of an attenuating material, such as, for example, tungsten. In FIG. 5, a transmitted x-ray beam from the first focal spot position 506 is illustrated as a flux triangle 510. In the illustrated embodiment, the flux triable 510 is asymmetric, sending more flux towards the right side of an imaged subject. A transmitted beam from the second focal spot position 508 is not shown but can be configured to send flux towards the left side of the imaged subject. While not shown in FIG. 5, shifting the focal spots positions up or down on the page can change the shape of the transmitted flux. For example, shifting the focal spot position up, closer to the collimator 504, can expand the width of the flux triangle 510 and shifting the focal spot position down, further from the collimator 504, can shrink the width of the flux triangle 510.

In some embodiments, the combination of the collimator 504 and the electromagnetic steering (e.g., using the electromagnetic actuator of the x-ray source) for a plurality of focal spots positions can be used to produce a desirable flux modulation. In some embodiments, the electromagnetic steering may be used to select a focal spot position from a plurality of focal spot positions, for example, a continuous range of focal spot positions. In some embodiments, combinations of focal spot positions can allow the CT system to achieve the desired flux in an averaged sense. For example, the focal spot position could be positioned first at the center, close to the collimator 504 to illuminate the entire field of view with a moderate level of flux. For the next gantry rotation angle, the focal spot position could be positioned off-center, far from the collimator 504, to add additional flux to a region of the sinogram where more photons is desired, such as a region of interest or a photon-starved region with high attenuation.

In some embodiments, the system shown in FIG. 5 can be used to realize similar radiation dose reduction benefits as the virtual bowtie concept associated with inverse geometry CT but with a conventional, third generation scanner. For example, by choosing an appropriately sized collimator width for slot 512, alternating between several points on the focal track 502, and oversampling locations on the focal track 502 where greater fluence is desired, a flux distribution similar to that possible with virtual bowtie can be generated. In some embodiments, a reconstruction method may be used that can combine data from these different positions appropriately to take advantage of this flux modulation.

In some embodiments, to achieve the level of flux control that is desired, it may be necessary either to position the slot collimator 504 very near the anode or to allow a wide range of electromagnetic deflection. However, most x-ray sources for CT only allow for a narrow amount of deflection. Accordingly, in some embodiments, it may be necessary to position the slot collimator 504 within the vacuum chamber of the x-ray source itself. In some embodiments, the slot collimator 504 may be configured to be retractable so that it is only used for appropriate clinical applications, when flux modulation is desired.

The following examples set forth, in detail, ways in which the present disclosure was evaluated and ways in which the present disclosure may be used or implemented, and will enable one of ordinary skill in the art to more readily understand the principles thereof. The following examples are presented by way of illustration and are not meant to be limiting in any way. Each example provides illustrative examples of values of the geometry of components of the system of FIG. 5.

In a first example, it may be assumed that the focal spot position is an ideal point at a center position and the collimator 504 is perfectly blocking. In this example, the slot collimator 504 may be positioned 10 mm from the focal spot with 3 mm opening width. Assuming a 600 mm x-ray source-isocenter distance, the nominal width of the flux triangle for the center focal spot position would be 18 cm wide at the isocenter position. The center 18 cm of the subject would therefore be completely illuminated, and the remainder of the subject would not receive any photons. In a second example, by alternating between two focal spot positions, for example, first focal spot position 506 and second focal spot position 508, that are 3 mm apart horizontally, two flux triangles that are 18 cm apart can be created. This can lead to uniform illumination of 36 cm of the subject. If the two focal spot positions 506 and 508 were 2 mm apart, then 30 cm of the object can be illuminated, with the central 6 cm receiving double fluence.

In a third example, it may be assumed instead that the slot collimator 504 opening 512 were only 1 mm wide, and that the x-ray source addressed a sequence of 9 focal spot positions (not shown in FIG. 5) spaced 1 mm apart. Each time a particular focal spot position is energized, a 6 cm region of the subject at isocenter may receive photons. Each of these 9 regions, each 6 cm wide, would be abutting. If the x-ray source addresses each of the 9 focal spot positions sequentially with equal frequency, the entire subject can be uniformly illuminated. However, in some embodiments, the x-ray source could also address each focal spot position in proportion to the amount of flux desired, spending more time or repeating focal spot positions where greater flux is desired. In this manner, a piecewise-constant flux profile, with 9 pieces each 6 cm wide, can be produced and the height of each piece would be proportional to the amount of time addressing that focal spot. In some embodiments, by further decreasing the slot collimator opening 512 and the distance between adjacent focal spot positions on the focal track 502 of the anode, the precision of the flux modulation could be further improved. This can provide flux modulation that is similar to the virtual bowtie in inverse geometry CT. However, this can also impose a larger flux penalty and may require faster sampling of the detector, faster deflection at the source, and greater heating of the anode in order to achieve adequate noise statistics and to mitigate viewstreak artifacts. For these reasons, in some embodiments a compromise may be considered where the size of the slot collimator is increased, and movement of the focal spot closer to and further from the collimator may be considered as is necessary to optimize the useful flux produced for the amount of tube heating that is permissible.

While the flux 510 is illustrated in FIG. 5 as a triangle, each focal spot position (e.g., first focal spot position 506) is not actually a point but has finite size, and penumbra effects as well as off-focal radiation can be significant and create some illumination of the entire detector. In most cases, these smoothing effects may be desirable to produce more gradually changing fluence profiles. In some embodiments, correction for off-focal radiation may be performed prior to reconstruction.

The present disclosure has described one or more preferred embodiments, and it should be appreciated that many equivalents, alternatives, variations, and modifications, aside from those expressly stated, are possible and within the scope of the invention.

The invention claimed is:

1. A method for acquiring x-ray data from a subject and generating a computed tomography (CT) image of the subject, the method comprising:

receiving, using a processor device, a set of illumination field data including an illumination field produced by each of a plurality of focal spot positions of an x-ray source;

selecting, using the processor device, at least one sequence of at least two illumination fields from the set of illumination field data based on at least one subject-specific parameter;

assigning an illumination field from the selected at least one sequence of at least two illumination fields to each gantry rotation angle in a plurality of gantry rotation angles;

acquiring x-ray data from a subject, using a detector array, for each gantry rotation angle in the plurality of gantry rotation angles using a focal spot position associated with the illumination field that is assigned to the gantry rotation angle, wherein the x-ray data includes a number of photons received by the detector array;

generating an image slice, using the processor device, based on the acquired x-ray data for each of the plurality of gantry rotation angles.

2. The method according to claim 1, further comprising selecting, using the processor device, the focal spot position for acquiring x-ray data from each gantry rotation angle of the plurality of gantry rotation angles based on the illumination field assigned to the gantry rotation angle.

3. The method according to claim 1, further comprising displaying the generated image slice on a display.

4. The method according to claim 1, wherein the x-ray source comprises an electromagnetic actuator system configured to direct a focal spot of the x-ray source to a focal spot position.

5. The method according to claim 1, wherein the at least one subject-specific parameter is a parameter associated with at least one of a subject-specific exposure or an image quality objective.

6. The method according to claim 5, wherein the at least one subject-specific parameter is one of organ radiation exposure, photon statistics, overall effective dose, or region of interest.

7. A system for acquiring x-ray data for a computed tomography (CT) image of a subject, the system comprising:

an x-ray source comprising an actuator system configured to energize one of a plurality of focal spot positions;

a grid assembly positioned in front of the x-ray source and comprising a plurality of grids, wherein each grid comprises a plurality of attenuating objects;

a processor device coupled to the x-ray source and programmed to:

receive a set of illumination field data including an illumination field produced by each of the plurality of focal spot positions of the x-ray source;

select at least one sequence of at least two illumination fields from the set of illumination field data based on at least one subject-specific parameter; and assign an illumination field from the selected at least one sequence of at least two illumination fields to each gantry rotation angle in a plurality of gantry rotation angles; and a detector array configured to receive x-ray data from the subject for each gantry rotation angle in the plurality of gantry rotation angles, the x-ray data for each gantry rotation angle based on the illumination field assigned to the gantry rotation angle and produced by an energized focal spot position associated with the assigned illumination field, wherein the x-ray data includes a number of photons received by the detector array.

8. The system according to claim 7, wherein the processor device is further programmed to generate an image slice based on the acquired x-ray data for each of the plurality of gantry rotation angles.

9. The system according to claim 8, further comprising a display coupled to the processor device and configured to display the generated image slice.

10. The system according to claim 7, wherein the x-ray source comprises an electromagnetic actuator system configured to direct a focal spot of the x-ray source to a focal spot position.

11. The system according to claim 7, wherein each grid in the plurality of grids is a planar grid.

12. The system according to claim 7, wherein the at least one subject-specific parameter is a parameter associated with at least one of a subject-specific exposure or an image quality objective.

13. The system according to claim 12, wherein the at least one subject-specific parameter is one of organ radiation exposure, photon statistics, overall effective dose, or region of interest.

14. A system for acquiring x-ray data for a computed tomography (CT) image of a subject, the system comprising:

an x-ray source comprising an actuator system configured to energize one of a plurality of focal spot positions;

a slot collimator positioned in front of the x-ray source and comprising an opening having a width;

a processor device coupled to the x-ray source and programmed to:

receive a set of illumination field data including an illumination field produced by each of the plurality of focal spot positions of the x-ray source;

select at least one sequence of at least two illumination fields from the illumination field data based on at least one subject-specific parameter; and assign an illumination field from the selected at least one sequence of at least two illumination fields to each gantry rotation angle in a plurality of gantry rotation angles; and a detector array configured to receive x-ray data from the subject for each gantry rotation angle in the plurality of gantry rotation angles, the x-ray data for each gantry rotation angle based on the illumination field assigned to the gantry rotation angle and produced by an energized focal spot position associated with the assigned illumination field, wherein the x-ray data includes a number of photons received by the detector array.

15. The system according to claim 14, wherein the x-ray source comprises an electromagnetic actuator system configured to direct a focal spot of the x-ray source to a focal spot position.

16. The system according to claim 14, wherein the processor device is further programmed to generate an image slice based on the acquired x-ray data for each of the plurality of gantry rotation angles.

17. The system according to claim 16, further comprising a display coupled to the processor device and configured to display the generated image slice.

18. The system according to claim 14, wherein the at least one subject-specific parameter is a parameter associated with at least one of a subject-specific exposure or an image quality objective.

19. The system according to claim 18, wherein the at least one subject-specific parameter is one of organ radiation exposure, photon statistics, overall effective dose, or region of interest.

* * * * *